US00PP24464P3

(12) United States Plant Patent
Roe

(10) Patent No.: US PP24,464 P3
(45) Date of Patent: May 20, 2014

(54) ***CITRUS RETICULATA* PLANT NAMED 'WG17'**

(50) Latin Name: *Citrus reticulata*
Varietal Denomination: WG17

(75) Inventor: Bill Roe, Eagle Lake, FL (US)

(73) Assignee: GJH LLC, Winter Haven, FL (US)

( * ) Notice: Subject to any disclaimer, the term of this patent is extended or adjusted under 35 U.S.C. 154(b) by 113 days.

(21) Appl. No.: 13/385,096

(22) Filed: Jan. 31, 2012

(65) Prior Publication Data

US 2013/0198916 P1 Aug. 1, 2013

(51) Int. Cl.
*A01H 5/00* (2006.01)

(52) U.S. Cl.
USPC ..... Plt./201; Plt./202

(58) Field of Classification Search
USPC ..... Plt./202, 201
See application file for complete search history.

*Primary Examiner* — June Hwu
(74) *Attorney, Agent, or Firm* — Cassandra Bright

(57) ABSTRACT

A new and distinct *Citrus reticulata* cultivar named 'WG17' is disclosed, characterized by having distinctive fruit of bright orange flesh that peels very easily with a meaty, crunchy texture. The fruit is physically large and tall in height and less oblate in shape. Additionally, the new variety produces fruit that takes ethylene gas without burning.

2 Drawing Sheets

Latin name of the genus and species: *Citrus reticulata.*
Variety denomination: 'WG17'.

BACKGROUND OF THE INVENTION

The new cultivar is a product of a planned crossing program in 2000 under the direction of the inventor, Bill Roe, a citizen of The United States. The inventor no longer has record of the seed parent, the pollen parent is the unpatented variety *Citrus reticulata* 'Honey Tang'.

This new variety was found in November 2006 in a commercial nursery in Winter Haven, Fla. Plants were first propagated by tissue culture in 2006 and subsequently grafted onto rootstocks US-897 and US-942. Development, evaluation, tissue culture and grafting all first took place at the inventor's commercial nursery in Winter Haven, Fla. USA. Subsequent evaluations of the variety have shown the characteristics to be true to type.

SUMMARY OF THE INVENTION

The cultivar 'WG17' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WG17' These characteristics in combination distinguish 'WG17' as a new and distinct *Citrus reticulata* cultivar:

1. Easy peeling fruit.
2. Develops bright orange external color.
3. Will take ethylene gas without burning.
4. Fruit has a crunchy internal texture, caused by very firm individual juice vesicles, similar to the texture of Pomelo.
5. Large fruit size.
6. Fruit produces a round, less oblate shape.
7. Early season development of high internal color.

COMPARISON TO PARENT VARIEITES

Seed Parent is unknown.

Plants of the new cultivar 'WG17' are similar to plants of the pollen parent, *Citrus reticulata* 'Honey Tang' in most horticultural characteristics, however, plants of the new cultivar 'WG17' produce fruit that matures 60-75 days earlier and is capable of taking ethylene gas without burning. Additionally, 'WG17' produces less juicy fruit than the unnamed pollen parent. Fruit of 'WG17' has lighter peel color than the parent. 'WG17' yields a fruit that is taller and less oblate as compared to the pollen parent.

COMMERCIAL COMPARISON

The new variety is best compared to the commercial variety, *Citrus reticulata* 'Robinson', unpatented. 'WG17' is similar to 'Robinson' in many horticultural characteristics however, 'WG17' produces larger fruit of lighter internal color, as well as fruit that holds on the tree with higher stability. Additionally, the new variety 'WG17' does not need cross pollination, whereas cross pollination is required in the variety 'Robinson.'

'WG17' can also be compared to *Citrus reticulata* 'Fallco', unpatented. The two varieties are similar in many horticultural characteristics, however 'WG17' produces fruit with lower acid and lighter internal color as well as easier peeling compared to 'Fallco'.

BRIEF DESCRIPTION OF THE PHOTOGRAPH

Figure 1:
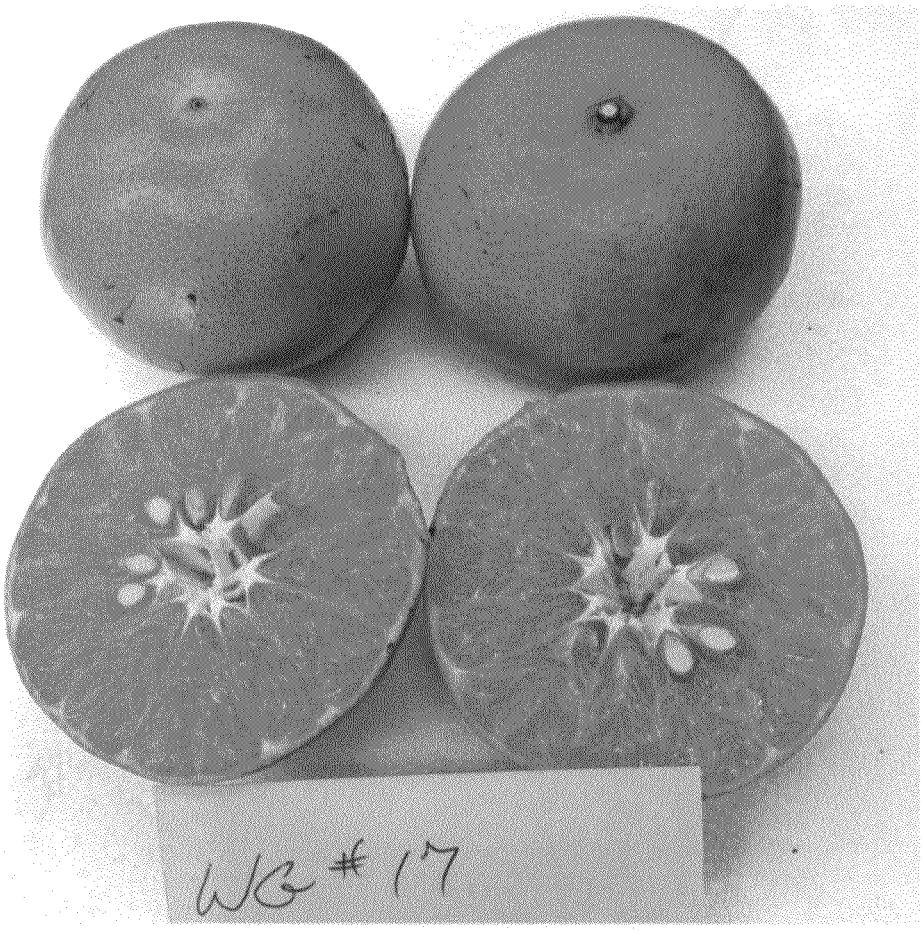

The accompanying photograph in FIG. 1 illustrates in full color examples of typical fruit harvested from 'WG17'.

Figure 2:
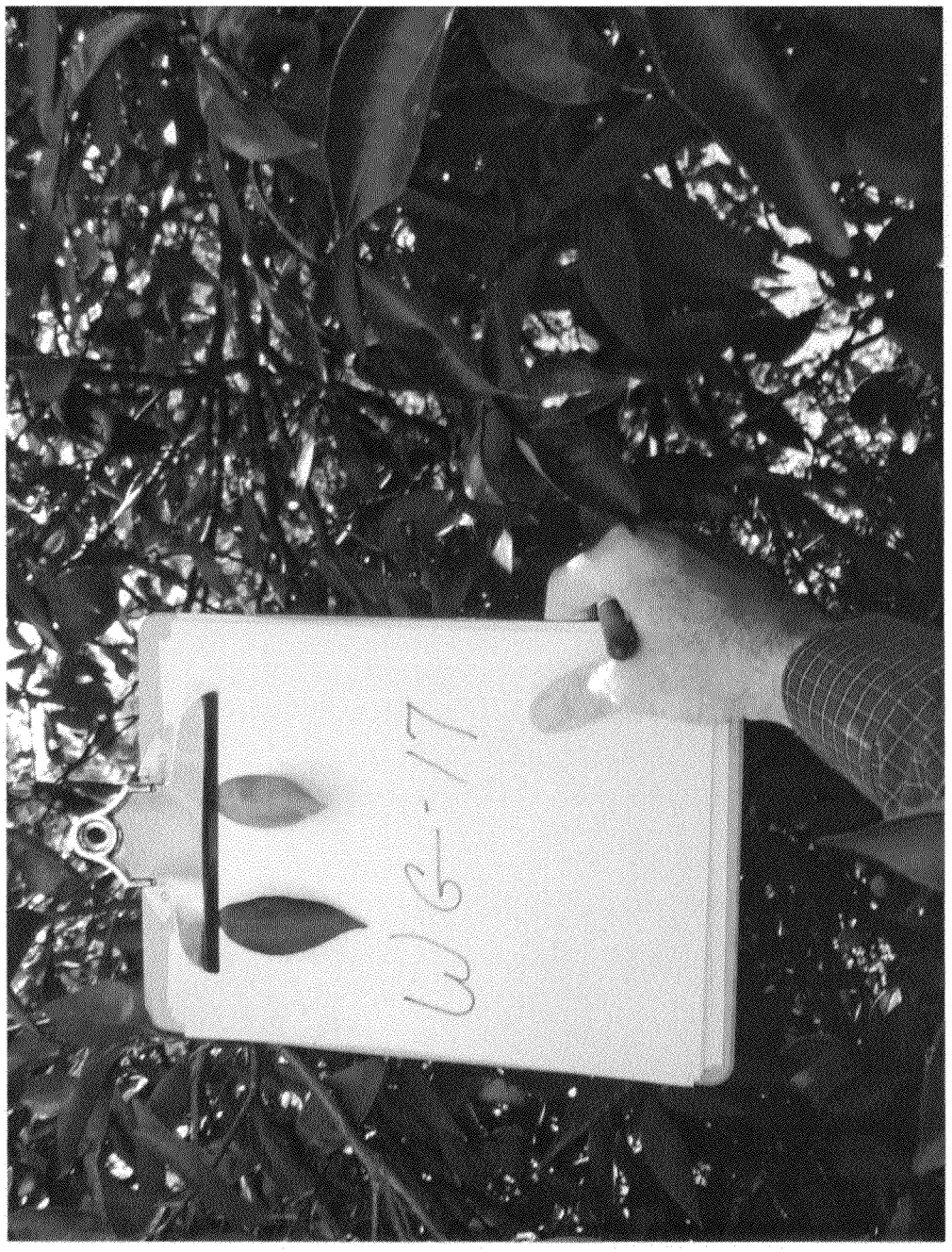

FIG. 2 illustrates in full color typical foliage of 'WG17'.

Photographs are taken of plants approximately 3 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'WG17' plants grown outdoors under commercial trial conditions in Winter Haven, Fla. USA. The growing temperature ranged from 4° C. to 37° C. during the day and −5° C. to 22° C. at night. Measurements and numerical values represent an average from the most typical specimens.

Botanical classification: *Citrus reticulata* 'WG17'.

PROPAGATION

'WG17' is typically grafted onto rootstock of *Citrus reticulata* US-897 and US-942

PLANT

Age of the plant described: Approximately 3 years.
Plant habit: Somewhat spreading form, with average canopy density.
Height: Approximately 200 cm.
Growth rate: Approximately 3 years to 200 cm.
Plant spread: Approximately 150 to 200 cm, depending on pruning.
Vigor: Good with heavy Spring flush and fruit-set with cross-pollination.
Length of primary lateral branches: Approximately 30-36 cm.
Quantity of lateral branches: 4-5.
Angle of lateral branches from main trunk: 155-165° degrees.
Branching arrangement: Alternate, branches exhibit only very moderate weeping.
Branch diameter: Average 3-4.5 cm.
Trunk texture: Smooth.
Trunk color: Near RHS Grey-Brown 199B.
Trunk diameter: Average 6.5-7.5 cm on a 3 year old plant.

FOLIAGE

Leaf:
- *Average length.*—6-11 cm. Average of 8.5-9 cm.
- *Average width.*—2.5-5 cm. Average of 4 cm.
- *Arrangement.*—Alternate.
- *Shape of blade.*—Ovate.
- *Apex.*—Acute.
- *Base.*—Attenuate.
- *Attachment.*—Stalked.
- *Margin.*—Smooth with ever so slight dentations.
- *Texture of top surface.*—Smooth.
- *Texture of under side.*—Slightly rough with pronounced center vein.
- *Color.*—Mature foliage upper side: Near RHS Green 139A. Mature foliage under side: Near RHS Green 141B.
- *Petiole.*—Length: Average length 1-1.5 cm. Pubescence: None. Color: Upper and lower surfaces near Yellow-Green 144B.

FLOWER

Inflorescence and flower type and habit: Single rotate flowers emerging from leaf axils.
Flower longevity on plant: Approximately 2 weeks.
Persistent or self-cleaning: Self-cleaning.
Bud:
- *Shape.*—Elongated, irregular sphere.
- *Length.*—Average 2.1 cm.
- *Diameter.*—0.9 cm.
- *Color.*—Near RHS White 155A.

Flower size:
- *Diameter.*—Average 3.1 cm.
- *Depth.*—Average 2.1 cm.

Corolla/petals:
- *Arrangement.*—Rotate.
- *Petal quantity.*—5.
- *Length.*—Average 1.7 cm.
- *Width.*—Average 0.9 cm.
- *Texture.*—Glabrous.
- *Apex.*—Acute.
- *Base.*—Blunt.
- *Shape.*—Oblong.
- *Margin.*—Entire.
- *Aspect.*—Flat.
- *Color.*—When opening: Upper surface: Near RHS White 155D. Lower surface: Near RHS White 155D. Fully opened: Upper surface: Near RHS White 155D. Lower surface: Near RHS White 155D.

Calyx/sepals:
- *Quantity per flower.*—5.
- *Shape.*—Linear, partially fused at base.
- *Length.*—Average 1.2 cm.
- *Width.*—0.3 cm.
- *Apex.*—Acute.
- *Base.*—Fused.
- *Margin.*—Entire.
- *Texture.*—Glabrous.
- *Color.*—Upper Surface: Near RHS Green 137A. Lower Surface: Near RHS Green 137A.

Pedicel:
- *Length.*—Average 1.7 cm.
- *Diameter.*—Average 0.25 cm.
- *Color.*—Near RHS Green 137A.
- *Orientation.*—Approximately 35 degree angle from leaf axil.
- *Texture.*—Glabrous.

Fragrance: Sweet, typical *Citrus* flower scent.

REPRODUCTIVE ORGANS

Stamens:
- *Number.*—Most commonly 12.
- *Filament length.*—Approximately 2.2 cm.

Anthers:
- *Shape.*—Globular.
- *Length.*—Approximately 0.2 cm.
- *Color.*—Near RHS Yellow-White 158A.
- *Pollen.*—Color: Near RHS Yellow 8C. Quantity: Moderate.

Pistil:
- *Number.*—1.
- *Length.*—Approximately 0.8 cm.
- *Style.*—Length: 0.6 cm. Color: Near RHS Green-Yellow 1D.
- *Stigma.*—Shape: linear. Color: Near RHS Yellow 8D. Ovary Color: RHS Green 143C.

FRUIT

Color exocarp: Near RHS Orange 28B.
Color mesocarp: Near RHS Orange N25D.
Flesh color: Near RHS Orange 28B.
Brix at consumption: 11.30.
Brix at harvest: 11.30. Acid 0.44 Ratio of 25.70.
Average weight: 230 grams.
Minimum weight: 180 grams.
Maximum weight: 280 grams.
Height: 5.8-6.4 cm. Average 6.2 cm.
Width: 7-7.7 cm. Average of 7.5.
Segment number per fruit: 11-12.
Segment size:
*Average width.*—1.5 cm.
*Average length.*—4.2 cm.
Fruit peduncle length: 1-2 cm.
Fruit peduncle width: 40-60 mm.
General shape: Not round as an orange, but not too oblate.
Fruit aroma: Tart, sweet.
Skin color at harvest: Near RHS Orange 28B.
Skin/rind thickness: Very thin: 15 mm.
Skin adherence to flesh at maturity: Exceptionally easy to peel. Peel zippers off.
Skin/rind texture: Extraordinarily smooth.
Harvest time:
*First harvest.*—October 10.
*Last harvest.*—December 1.
Overall cropping quantity: Crops heavily with huge fruit.
Mature seed color: Near RHS Greyed-Yellow 161D.
Quantity seed per fruit: An average sample of more than 100 fruits gives an average of less than 2 seeds per fruit.
Seed shape: Ovoid.
Seed length: 10-13 mm. Average of 12 mm.
Seed width: 5.5-7 mm.
Other: Seeds aborted.

OTHER CHARACTERISTICS

Storage life: Storage life is a minimum of 60 plus days at 2° C.
Disease/pest resistance: 'WG17' has been observed to be susceptible to Tangerine scab, *Elsinoë fawcettii*. No other susceptibility nor resistance observed.
Other fruit features: Takes ethylene gas very well. Fruit possesses a very meaty and deep colored internal flesh. Fruit holds on tree very well. Initially some dryness arises at the fruit stem end, as the fruit matures, this dryness does not develops further. 'WG17' has a crunchy internal character, due to firm juice vesicles, and is somewhat atypical of Florida fruit in that it has juice content reminiscent of Mediterranean climate fruit.
Shipping quality: The inventor measures shipping quality with two categories: Perishability; meaning damage caused by clear rot, blue-green mold and stem end rot. Misshapen fruit; Damage to the fruit shape when packed in a commercial 35 to 40 pound shipping box. 'WG17' produces a very firm fruit with a tight skin. The fruit does not become misshapen during shipment, and has good resistance to the perishability factors listed above. 'WG17' produces a very firm fruit ideal for interstate shipment in commercial shipping boxes.
Temperature tolerance: Tolerates low temperatures to approximately −5° C. without negative effects, tolerates high temperatures to approximately 37° C. without negative effects.

What is claimed is:

1. A new and distinct cultivar of *Citrus reticulata* plant named 'WG17' as herein illustrated and described.

* * * * *